United States Patent [19]

Onishi et al.

[11] Patent Number: 5,547,472
[45] Date of Patent: Aug. 20, 1996

[54] CATHETER WITH MEDICAMENT INJECTION PORES

[75] Inventors: Makoto Onishi; Kenji Ishikawa, both of Kanagawa, Japan

[73] Assignee: Terumo Kabushiki Kaisha, Tokyo, Japan

[21] Appl. No.: 375,589

[22] Filed: Jan. 19, 1995

[30] Foreign Application Priority Data

Jan. 20, 1994 [JP] Japan .................... 6-004867

[51] Int. Cl.⁶ .................................. A61M 11/00
[52] U.S. Cl. .................. 604/93; 604/48; 604/96; 604/264
[58] Field of Search ............ 604/96, 27, 30, 604/31, 48, 50, 54, 93, 245, 246, 247, 264, 280

[56] References Cited

U.S. PATENT DOCUMENTS

| | | | |
|---|---|---|---|
| 4,280,500 | 7/1981 | Ono ........................................ | 604/280 |
| 4,767,400 | 8/1988 | Miller et al. ........................ | 604/280 X |
| 4,994,033 | 2/1991 | Shockey et al. .................... | 604/96 X |
| 5,049,132 | 9/1991 | Shaffer et al. ...................... | 604/96 X |
| 5,087,244 | 2/1992 | Wolinsky et al. . | |
| 5,098,381 | 3/1992 | Schneider . | |
| 5,141,499 | 8/1992 | Zappacosta ......................... | 604/280 X |
| 5,146,916 | 9/1992 | Catalani .............................. | 604/264 X |
| 5,213,576 | 5/1993 | Abiuso et al. . | |
| 5,232,444 | 8/1993 | Just et al. ........................... | 604/96 |
| 5,236,413 | 8/1993 | Feiring ............................... | 604/96 X |
| 5,254,089 | 10/1993 | Wang .................................. | 604/96 |
| 5,286,254 | 2/1994 | Shapland et al. .................... | 604/96 X |
| 5,306,250 | 4/1994 | March et al. ........................ | 604/104 |
| 5,318,531 | 7/1994 | Leone ................................. | 604/96 |
| 5,336,177 | 8/1994 | Marcus ............................... | 604/264 X |
| 5,336,178 | 8/1994 | Kaplan et al. ...................... | 604/280 X |
| 5,389,074 | 2/1995 | Parker et al. ....................... | 604/54 X |

FOREIGN PATENT DOCUMENTS 2-283380  11/1990  Japan .

*Primary Examiner*—Corrine M. McDermott
*Assistant Examiner*—N. Kent Gring
*Attorney, Agent, or Firm*—Burns, Doane, Swecker & Mathis, L.L.P.

[57] ABSTRACT

A catheter or balloon catheter includes a tube or balloon which is provided with a plurality of pores. A stimulus-responsive polymer is attached to the pores so that fluid transmission through the pores is controllable by a stimulus such as a change of pH, composition, and temperature. The catheter can administer a necessary limited amount of medicament to a locally limited site of a blood vessel only when necessary.

6 Claims, 2 Drawing Sheets

CATHETER WITH MEDICAMENT INJECTION PORES

BACKGROUND OF THE INVENTION

1. Field of the Invention

This invention generally relates to a catheter and more particularly, to a catheter for use in treating blood vessels or other body organs with medicaments.

2. Prior Art

For the treatment of various diseases, it is often desired to administer a high concentration of medicament to lesions in human body organs or vessels. In an attempt to provide an effective amount of medicament to the lesion through general oral administration and phleboclysis, some medicaments would produce side effects of giving so serious damage to other sites as to bring the patient in danger or causing chill and pain to the patient. Despite their superior pharmaceutical effect, these medicaments cannot be applied to the lesion in practice.

For the treatment of intrinsic intravascular stenosis, typically coronary stenosis, angioplasty using dilating balloon catheters has been widespread over decades. See Gruntig, The New England Journal of Medicine, Vol. 301, No. 2, 12/6/1979, pages 61–68. The angioplasty is a therapy of percuteneohsly inserting a balloon catheter into the coronaria until the balloon reaches a stenosis, and inflating the balloon to dilate the stenosis. It is less invasive and hence, imposes a less physical burden to the patient as compared with surgical operation. One outstanding problem of the angioplasty is relatively high recurrence of once dilated intravascular stricture. To prevent recurrence, attempts are made to administer to the focus or dilated vessel inner wall various anti-restenosis agents, anti-thrombotic agents, thrombolytic agents, decalcifying agents, anti-calcifying agents, certain cytokines, cytostatic agents, and vectors for controlling the propagation of smooth muscle cells.

Japanese Patent Application Kokai (JP-A) No. 283380/1990 discloses a balloon which is perforated with pores for injecting medicament. This balloon fails to administer an appropriate effective amount of medicament to the lesion under desirable conditions since the size of medicament injecting pores cannot be controlled. For example, the balloon fails to accommodate a variety of strictures of different lesion where it is desired to administer medicament fluid with the balloon inflated under a low pressure or where medicament administration under a high pressure is not desired.

SUMMARY OF THE INVENTION

An object of the present invention is to provide a catheter for administering a medicament to a locally limited site of an organ having a lumen, typically a blood vessel. Another object of the invention is to provide a catheter having medicament injecting pores whose diameter is controllable by an external stimulus so that a necessary limited amount of medicament can be administered to a locally limited site only when necessary.

The present invention provides a catheter including a tube or a balloon catheter including a balloon. The tube or balloon is perforated with a plurality of pores which extend throughout the tube or balloon wall. Means is associated with the pores for controlling the pore diameter. Specifically, a polymer capable of effecting a structural change in response to a stimulus is attached to the pores. Then fluid transmission from the tube or balloon interior to the exterior through the pores is controllable by the stimulus.

Preferably, the polymer using in this invention may be changed in its chemical structure by a stimulus to have fluid permeability or transmission ability.

Preferably the stimulus is selected from pH, ion, solvent composition, chemical substance, heat, electricity and light such as ultraviolet radiation.

BRIEF DESCRIPTION OF THE INVENTION

The features and advantages of the invention will be more fully understood by reading the following description of one preferred embodiment taken in conjunction with the drawings.

DESCRIPTION OF THE PREFERRED EMBODIMENT

The catheter of the invention is used for administering medicament to a lesion in a blood vessel or live tissue for treatment or prophylaxis. Although the following description refers to the treatment of coronary stenosis as found in ischemic heart diseases such as myocardinal infarction, the "lesion in a blood vessel or live tissue" is not limited thereto. Also the shape of the catheter is not limited to the embodiment illustrated herein. Both a tubular catheter and a balloon catheter having a balloon at the distal end are included within the scope of the invention.

Therapies currently used for the prophylaxis and treatment of intravascular stenosis includes an anti-thrombotic therapy (e.g., thrombolytic therapy, anticoagulant therapy, and antiplatelet therapy) and a therapy of using a catheter having a balloon at its distal end and dilating the stenosis with the balloon, which is known as percutaneous transluminal coronary angioplasty (PTCA). The catheter of the invention is advantageously used for the treatment of vasostenosis by either therapy.

Figure 1:
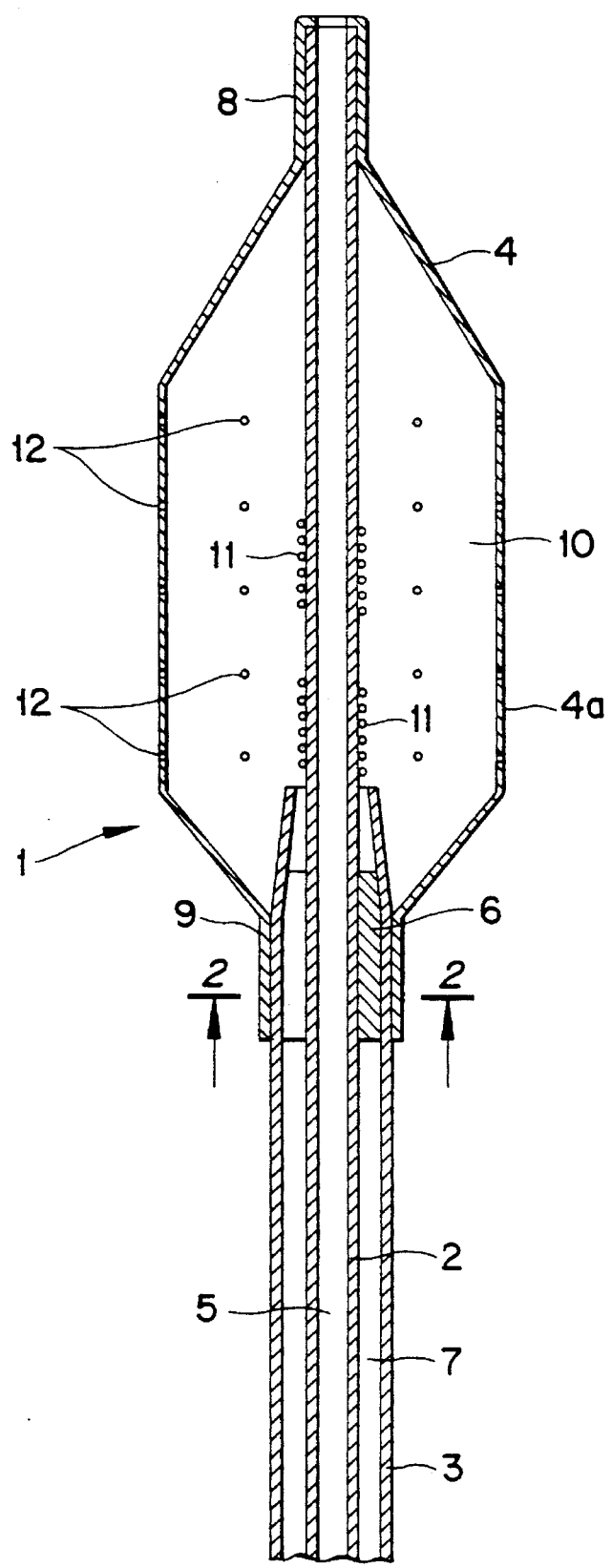
FIG. 1 is an axial cross-sectional view of a distal portion of a medicament administering catheter according to one embodiment of the invention.
Figure 2:
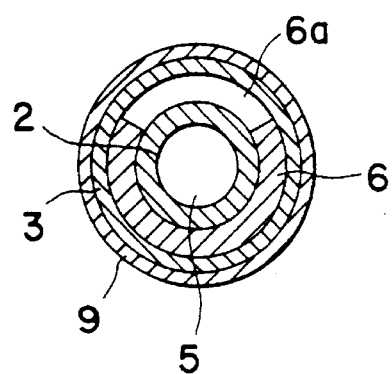
FIG. 2 is a transverse cross-sectional view of the catheter taken along lines 2 in FIG. 1.

Referring to FIG. 1, there is illustrated a distal portion of a balloon catheter 1 including a catheter tube consisting of an inner tube 2 and an outer tube 3 and a balloon 4 attached to a distal end (upper end in FIG. 1) of the catheter tube. The inner tube 2 defines a first lumen 5 which is open at distal and proximal ends. A guide wire (not shown) is received for free insertion in the first lumen 5. The outer tube 3 encloses the inner tube 2 and has a distal end which is retracted a certain distance from the distal end of the inner tube 2. A second lumen 7 is defined between the inner surface of the outer tube 3 and the outer surface of the inner tube 2. The second lumen 7 at its distal end is in fluid communication with a rear end portion of the interior of the balloon 4. A suitable liquid which may contain an anti-thrombos medicament and vasographic agent is passed through the second lumen 7 into the balloon 4 for inflating the balloon 4. The distal end of the outer tube 3 is fixedly secured to the inner tube 2 in such a manner that the second lumen 7 is not blocked. More particularly, a filler member 6 is interposed between the inner and outer tubes 2 and 3 for securing the tubes. As shown in FIG. 2, the filler member 6 is an arcuate member with a cutout 6a through which the second lumen 7 is in fluid communication with the interior of the balloon 4.

The balloon 4 is a foldable or contractible member, that is, can be held in a folded state flush on the outer periphery of the inner tube 2 when contracted. The balloon 4 includes a central section 4a which is substantially cylindrical and has a substantially equal diameter when inflated so that the stricture in a blood vessel can be expanded thereby. The balloon 4 includes rear and front tapered portions and rear and front end portions 9 and 8. The rear end portion 9 is secured to the distal end portion of the outer tube 3 in a liquid tight manner and the front end portion 8 is secured to the distal end portion of the inner tube 2 in a liquid tight manner so that an inflation space 10 is defined between the inner surface of the balloon 4 and the outer surface of the inner tube 2. The inflation space 10 at its rear end portion is in fluid communication with the second lumen 7 through the cutout 6a in the filler member 6. The balloon 4 is provided with a plurality of pores 12 which extend through a balloon wall for providing fluid transmission through the pores. The surface of each pore has attached or bonded thereto a polymer which effects a structural change in response to an external stimulus. When it is desired to expand the vessel stricture, with the pores 12 throttled, the liquid under pressure is introduced into the balloon 4 through the second lumen 7 to inflate the balloon 4. When it is desired to administrate a medicament to the stricture, a stimulus is applied to the pores 12, more specifically to the polymer, to increase the pore diameter, allowing the medicament to be released from the balloon interior to the exterior or vessel.

Further the inner tube 2 is provided on the outer surface with a reinforcement 11 in the form of a coil spring. In order that the position of the balloon 4 is readily confirmed under X-ray observation, two coil springs 11 are located around the outer surface of the inner tube 2 at a center position corresponding to the center and a rear position near the rear tapered portion of the balloon 4 or the distal end of the outer tube 3. A radiopaque platinum marker may be used instead of the coil springs.

Figure 3:
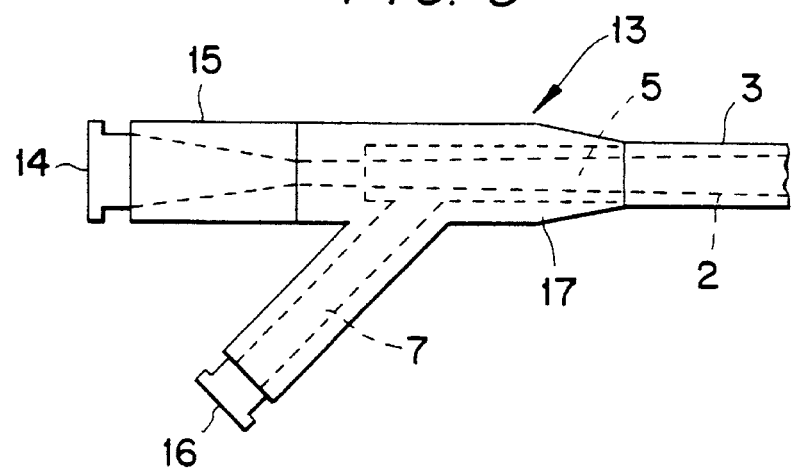
FIG. 3 is a schematic view of a proximal portion of the catheter according to one embodiment of the invention.

FIG. 3 illustrates a proximal portion of the catheter 1 including a branch hub 13. The branch hub 13 includes an inner tube hub 15 fixedly secured to the inner tube 2 and having a first opening 14 which defines a guide wire port in communication with the first lumen 5 of the inner tube 2. The branch hub 13 also includes an outer tube hub 17 fixedly secured to the outer tube 3 and having a second opening 16 which defines an injection port in fluid communication with the second lumen 7. The inner and outer tube hubs 15 and 17 are fixedly joined to form the integral branch hub 13. The branch hub 13 is preferably manufactured of a thermoplastic resin such as polycarbonates, polyamides, polysulfones, polyarylates, and methacrylate-butylene-styrene copolymers.

Figure 4:
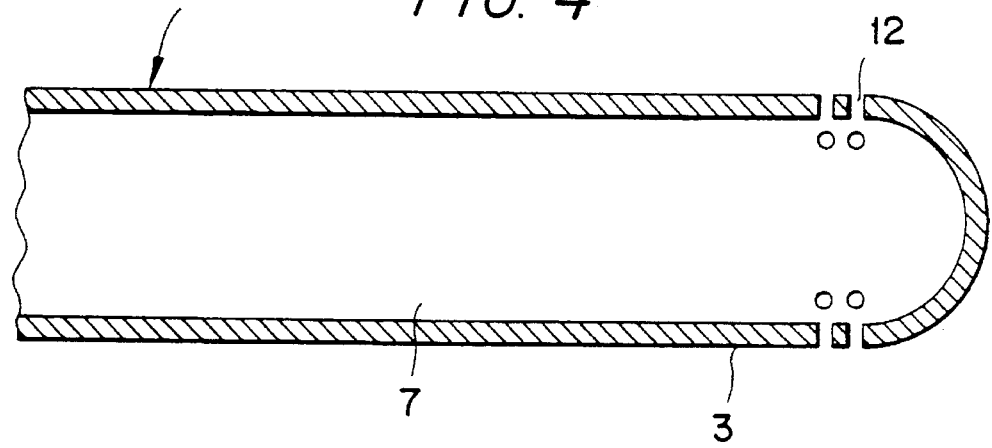
FIG.4 is an axial cross-sectional view of a catheter according to another embodiment of this invention.

FIG. 4 illustrates a catheter 20 having an outer tube 3. The outer tube 3 is provided in the distal end with a plurality of pores 12 which extend through an outer tube wall for providing fluid transmission through the pores.

The medicament used herein is any medicament which is used for the treatment and prophylaxis of lesions. For vasoconstriction, thrombolytic agents such as urokinase, prourokinase, streptokinase, and plasminogen activators are used as well as heparin, warfarin, aspirin, and smooth muscle cytostatic agents. For malignant tumor, carcinostatic agents are administered.

The catheter tube and balloon may be made of any desired material. Useful materials of which the tube and balloon are made include olefinic polymers such as polyethylene, polypropylene, polybutene, and polybutadiene and copolymers, halides and ionomers thereof; condensed polymers such as various polyesters and polyamides and copolymers thereof with polyethers; and polyurethanes. The material is not limited to polymers. Catheter tubes and balloons containing a pipe of super-elastic alloy or a coil and mesh of metal are also useful.

In general, the components of the catheter have the following dimensions though the invention is not limited thereto. The inner tube 2 has an outer diameter of about 0.30 to 2.50 mm, preferably about 0.40 to 2.40 mm and an inner diameter of about 0.20 to 2.35 mm, preferably about 0.25 to 1.80 mm. The outer tube 3 has an outer diameter of about 0.50 to 4.30 mm, preferably about 0.60 to 4.00 mm and an inner diameter of about 0.40 to 3.80 mm, preferably about 0.50 to 3.00 mm. The balloon 4, when inflated, defines a cylindrical shape having an outer diameter of about 1.00 to 35.00 mm, preferably about 1.50 to 30.00 mm and a length of about 3.00 to 80.00 mm, preferably about 10.00 to 75.00 mm. The balloon has an overall length of about 5.00 to 120.00 mm, preferably about 15.00 to 100.00 mm.

The filler member 6 interposed between the inner and outer tubes 2 and 3 of the catheter tube is preferably made of a material which well adheres to the inner and outer tubes 2 and 3. For the inner and outer tubes 2 and 3 made of polyolefinic material, for example, polyethylene (PE) and ethylene vinyl acetate (EVA) are preferably used. The filler member 6 has an axial length of about 1 to 10 mm, preferably about 2 to 8 mm. As shown in the cross section of FIG. 2, the filler member 6 has an arcuate shape which should preferably extend at least ⅓, especially at least ½ of the entire circumference.

No particular limit is imposed on the shape of the pores perforated in the catheter tube or balloon. The pores may be of circular, oval, triangular, tetragonal, pentagonal, hexagonal, star or slit shape. The size of the pores required on medicament injection is preferably about 0.1 to 1,000 μm although the size varies with a particular purpose, objective site, the concentration and viscosity of medicament fluid and other factors.

The pores may be distributed locally or broadly. When the pores may be distributed locally, the medicament can be applied locally to cause the agent to penetrate into the localized portion of a patient.

The catheter tube or balloon is perforated with a plurality of pores by any desired technique, for example, laser machining, accelerated particle machining, electric discharge machining, stretching, phase separation, and wet re-coagulation. Using an excimer laser, for example, pores of a controlled diameter can be perforated at any desired position.

According to the invention, a polymer capable of effecting a structural change in response to a stimulus, which is often referred to as stimulus-responsive polymer, is attached to the pores by any desired method such as grafting, crosslinking insolubilization, coating, and surface polymerization. A suitable method is selected in accordance with the type of polymer. The polymer need not be attached to only the pores. It suffices that the pores are blocked with the polymer when lubricated. For example, the polymer may entirely cover the region of a tube or balloon surface where pores are distributed. When the grafting method is used, polymerization is effected at the tube or balloon surface to form a stimulus-responsive polymer in situ or a stimulus-responsive polymer is previously synthesized and then bonded to the tube or balloon surface. The stimulus-responsive polymer may be bonded to the tube or balloon surface by effecting crosslinking reaction between polymer units. Alternatively, the stimulus-responsive polymer is insolubilized and then coated to the tube or balloon surface.

The stimulus which can cause a structural change to the polymer in the pores is selected from pH, ion, solvent composition, chemical substance, heat, electricity and light such as ultraviolet radiation. The structural change of polymer is swelling and contraction. The invention utilizes the nature of polymer that an external stimulus triggers a reversible structural change between a solvated state and a desolvated state.

For example, a polymeric electrolyte gel is known to undergo a structural change owing to an osmotic pressure change by electrolyte ions in the polymer chain and interaction of electrolyte ions with a solvent. Then the polymeric electrolyte gel undergoes reversible contraction in response to a change of pH, solvent composition and ion concentration. An electric stimulus (in terms of potential, voltage and current) can be effectively utilized for the polymer's contraction response since it can bring a local change of pH or ion concentration. Among non-ionic polymers, polymers and copolymers of vinyl methyl ether and N-isopropylacrylamide undergo a change between hydrophilic and hydrophobic states in response to heat and provide a contraction response in an aqueous solvent. Then by utilizing heat generation by electric resistance or heat of mixing, the effective diameter of pores the can be changed. A stimulus given by a chemical substance is such that polymer chains swollen in pores are contracted if a complex is formed by utilizing hydrogen bonds or the like. For example, if a carboxylic polymer swollen in pores is contacted with an agent containing a polyether, the polycarboxylic acid reacts with the polyether to form a high molecular weight complex with concomitant contraction, resulting in the pores increasing an open passage for medicament fluid.

EXAMPLE

Examples of the present invention are given below by way of illustration and not by way of limitation.

Example 1

A balloon was formed of polyethylene terephthalate (PET) which would have an outer diameter of 2.5 mm and a wall thickness of 20 to 40 μm when inflated under an internal pressure of 4 atmospheres. Using an excimer laser (Lumonix® manufactured by Sumitomo Heavy Machinery K.K.), the balloon was perforated with 400 pores of 34×34 μm square cross section. The perforated PET balloon on the surface was subject to glow discharge treatment to create radicals and then to graft polymerization in a 50% acetone solution of methacrylic acid (MAA), obtaining the perforated balloon having MAA graft polymerized to the surface. Using this perforated balloon, a balloon catheter as shown in FIG. 1 was manufactured..

Through the second lumen 7 between the inner and outer tubes 2 and 3 of the balloon catheter 1 (through which a contrast agent is normally injected), a citric acid buffer solution at pH 8.0 was introduced into the balloon 4 under an internal pressure of 4 atmospheres to inflate the balloon. At this point, no outflow of the buffer solution through the pores was visually observed.

Next, the buffer solution was removed by suction and instead, a medicament fluid (heparin-added citric acid buffer solution) at pH 6.0 was introduced into the balloon to inflate the balloon. It was observed that the medicament fluid slowly flowed out of the balloon through the pores.

Example 2

An aspirin-added solution was introduced into the balloon catheter prepared in Example 1 to inflate the balloon. No outflow of the solution through the pores was visually observed. Next, the solution was removed by suction and instead, a solution of the same composition, but containing 0.2% of polyethylene glycol (weight average molecular weight Mw 2000) was introduced into the balloon to inflate the balloon. The solution slowly flowed out of the balloon.

Example 3

A balloon was formed of radiation-crosslinked polyethylene which would have an outer diameter of 2.5 mm when inflated. Using an excimer laser (Lumonix® manufactured by Sumitomo Heavy Machinery K.K.), the balloon was perforated with 400 square pores of 30×+μm in cross section. The perforated polyethylene balloon on the surface was subject to glow discharge treatment to create radicals and then to graft polymerization of diethylacrylamide and acrylamide in a 70% ethanol solution, obtaining the perforated balloon having the copolymer graft polymerized to the surface. Using this perforated balloon, a balloon catheter as shown in FIG. 1 was manufactured.

As in Example 1, physiological saline was introduced into the catheter under an internal pressure of 4 atmospheres to inflate the balloon. No outflow of saline through the pores was visually observed. Next, the saline was removed by suction and instead, a 2:3 mixture of physiological saline having aspirin dissolved therein and dimethylsulfoxide was introduced into the catheter to inflate the balloon. It was observed that the solution slowly flowed out of the balloon.

Example 4

A perforated balloon of polyethylene having an inflated outer diameter of 2.5 mm was prepared as in Example 3 and subject to glow discharge treatment to create radicals. Graft polymerization of isopropylmethacrylamide and butyl methacrylate (14:1) in a 70% ethanol solution was effected on the balloon surface. Using this perforated balloon, a balloon catheter as shown in FIG. 1 was manufactured.

As in Example 1, a medicament (physiological saline having aspirin dissolved therein) at 35° C. was introduced into the catheter under an internal pressure of 4 atmospheres to inflate the balloon. No outflow of the medicament through the pores was visually observed. Next, the medicament was removed by suction and instead, the same medicament heated at 42° C. was introduced into the catheter to inflate the balloon. The medicament slowly flowed out of the balloon.

There has been described a catheter which allows a controlled amount of medicament to pass therethrough to the exterior. It is a medicament administering catheter which can administer a necessary limited amount of medicament to a locally limited site only when necessary. Especially in the case of a PTCA dilating catheter including a balloon having pores for medicament injection, the catheter can afford medicament administration to a variety of strictures of different lesion under various conditions, for example, when medicament is to be administered to a stenosis in a blood vessel with the balloon inflated under low pressure or when medicament administration is undesired even with the balloon inflated under high pressure. The catheter of the invention is thus advantageous for the treatment and prophylaxis of vasoconstriction.

Although some preferred embodiments have been described, many modifications and variations may be made thereto in the light of the above teachings. It is therefore to be understood that within the scope of the appended claims, the invention may be practiced otherwise than as specifically described.

We claim:

1. A catheter including a tube having a tube wall, said tube comprising a first polymer and having a plurality of pores extending through said tube wall, said pores having associated therewith a second polymer which is different from the first polymer and which undergoes a structural change upon contact with a fluid introduced into the tube that has a physical or a chemical property that induces said structural change of said second polymer to thereby enable a selective transmission of the fluid through said tube wall.

2. A catheter according to claim 1, wherein said physical or chemical property of the fluid that induces said structural change of said second polymer is at least one member selected from pH, ion concentration, composition of the fluid, and temperature.

3. A catheter according to claim 1, wherein said second polymer is selected from a polymethacrylic acid, a diethylacrylamide-acrylamide copolymer, polyisopropylacrylamide, polyisopropylmethacrylamide, and polybuthyl methacrylate.

4. A balloon catheter including a balloon, said balloon comprising a first polymer and having a plurality of pores extending through said balloon, said pores having associated therewith a second polymer which is different from the first polymer and which undergoes a structural change upon contact with a fluid introduced into the balloon that has a physical or a chemical property that induces said structural change of said second polymer to thereby enable a selective transmission of the fluid through said balloon.

5. A catheter according to claim 4, wherein said physical or chemical property of the fluid that induces said structural change of said second polymer is at least one member selected from pH, ion concentration, composition of the fluid, and temperature.

6. A balloon catheter according to claim 4, wherein said second polymer is selected from a polymethacrylic acid, a diethylacrylamide-acrylamide copolymer, polyisopropylacrylamide, polyisopropylmethacrylamide, and polybuthyl methacrylate.

* * * * *

UNITED STATES PATENT AND TRADEMARK OFFICE
CERTIFICATE OF CORRECTION

PATENT NO. : 5,547,472
DATED : August 20, 1996
INVENTOR(S) : Makoto ONISHI, et al.

It is certified that error appears in the above-indentified patent and that said Letters Patent is hereby corrected as shown below:

In Column 1 line 27 delete "percuteneohsly" and insert --percuteneously--.

In Column 6, line 24, delete "30X+$\mu$m" and insert --30 × 30$\mu$m--.

Signed and Sealed this

Twenty-sixth Day of November 1996

BRUCE LEHMAN

Attest:

Attesting Officer           Commissioner of Patents and Trademarks